(12) United States Patent
Bartels

(10) Patent No.: US 8,409,628 B2
(45) Date of Patent: Apr. 2, 2013

(54) METHODS AND COMPOSITIONS FOR OXYGENATION OF SKIN TO TREAT SKIN DISORDERS

(75) Inventor: Jennifer Bartels, Hammond, LA (US)

(73) Assignee: Penguin IP Holdings, Inc., Hammond, LA (US)

( * ) Notice: Subject to any disclaimer, the term of this patent is extended or adjusted under 35 U.S.C. 154(b) by 469 days.

(21) Appl. No.: 12/700,375

(22) Filed: Feb. 4, 2010

(65) Prior Publication Data

US 2011/0189307 A1  Aug. 4, 2011

(51) Int. Cl.
*A01N 59/08* (2006.01)
*A61K 33/14* (2006.01)

(52) U.S. Cl. ........................................................ 424/677

(58) Field of Classification Search .................. None
See application file for complete search history.

(56) References Cited

U.S. PATENT DOCUMENTS

| | | | |
|---|---|---|---|
| 4,346,709 A | 8/1982 | Schmitt | |
| 4,719,111 A | 1/1988 | Wilson | |
| 4,778,679 A | 10/1988 | Silvetti | |
| 4,847,083 A | 7/1989 | Clark | |
| 4,868,169 A | 9/1989 | O'Laughlin | |
| 4,992,476 A | 2/1991 | Geria | |
| 5,037,648 A | 8/1991 | Joiner | |
| 5,378,468 A | 1/1995 | Suffis | |
| 5,512,274 A | 4/1996 | Phinney | |
| 5,516,517 A | 5/1996 | Gardner | |
| 5,547,661 A | 8/1996 | Sun | |
| 5,549,887 A | 8/1996 | Galleguillos | |
| 5,632,974 A | 5/1997 | Galleguillos | |
| 5,672,340 A | 9/1997 | Sun | |
| 5,833,965 A | 11/1998 | Sun | |
| 6,103,245 A | 8/2000 | Clark | |
| 6,121,317 A | 9/2000 | Wu | |
| 6,159,480 A | 12/2000 | Tseng | |
| RE37,274 E | 7/2001 | Gardner | |
| 6,423,323 B2 | 7/2002 | Neubourg | |
| 6,437,165 B1 | 8/2002 | Mandala | |
| 6,558,695 B2 | 5/2003 | Luo | |
| 6,562,368 B2 | 5/2003 | Hsu | |
| 6,565,879 B1 | 5/2003 | Luo | |
| 6,573,282 B1 | 6/2003 | Yaksh | |
| 6,586,000 B2 | 7/2003 | Luo | |
| 6,602,912 B2 | 8/2003 | Hsu | |
| 6,632,796 B1 | 10/2003 | Hamdi | |
| 6,632,836 B1 | 10/2003 | Baker | |
| 6,645,520 B2 | 11/2003 | Hsu | |
| 6,649,145 B2 | 11/2003 | McGrath | |
| 6,649,629 B2 | 11/2003 | Bandarage | |
| 6,656,928 B1 | 12/2003 | McCadden | |
| 6,673,363 B2 | 1/2004 | Luo | |
| 6,682,732 B1 | 1/2004 | Blake | |
| 6,706,724 B2 | 3/2004 | Khanapure | |
| 6,719,997 B2 | 4/2004 | Hsu | |
| 6,805,875 B2 * | 10/2004 | Bartels | 424/401 |
| 6,821,523 B2 | 11/2004 | Maibach | |
| 6,825,185 B2 | 11/2004 | Khanapure | |
| 6,835,392 B2 | 12/2004 | Hsu | |
| 6,846,837 B2 | 1/2005 | Maibach | |
| 6,905,675 B2 | 6/2005 | Shacknai | |
| 6,936,627 B2 | 8/2005 | Garvey | |
| 6,943,197 B2 | 9/2005 | Maibach | |
| 7,014,630 B2 | 3/2006 | Rosati | |
| 7,018,464 B2 | 3/2006 | Noguchi | |
| 7,067,553 B2 | 6/2006 | Suh | |
| 7,071,170 B2 | 7/2006 | Kaneko | |
| 7,083,806 B2 | 8/2006 | Rippon | |
| 7,129,251 B2 | 10/2006 | Garvey | |
| 7,256,205 B2 | 8/2007 | Garvey | |
| 7,303,759 B2 | 12/2007 | Mershan | |
| 7,338,670 B2 | 3/2008 | Dewhirst | |
| 7,427,595 B1 | 9/2008 | Zhu | |
| 7,514,432 B2 | 4/2009 | Leblond | |
| 7,540,283 B2 | 6/2009 | Loori | |
| 7,557,087 B2 | 7/2009 | Rothbard | |
| 7,563,224 B2 | 7/2009 | Puchek | |
| 7,625,575 B2 | 12/2009 | Wagoner | |
| 2004/0166183 A1 * | 8/2004 | Ruseler-van Embden et al. | 424/773 |
| 2008/0138451 A1 | 6/2008 | Wagoner | |

OTHER PUBLICATIONS

Euxyl PE 9010—Jul. 2008.*
Laks, Hillel, et al., The Relationship Between Muscle Surface pH and Oxygen Transport, Ann Surg., Feb. 1976, v.183(2), pp. 193-198.
International Search Report of corresponding PCT Application PCT/US2011/022184, Oct. 24, 2011.

* cited by examiner

*Primary Examiner* — James H Alstrum Acevedo
*Assistant Examiner* — Thor Nielsen
(74) *Attorney, Agent, or Firm* — Todd L. Juneau

(57) ABSTRACT

Methods and compositions for treating wounds, decubitus ulcers, diaper rash, burns, abrasions, and other irritations and relevant injuries are provided. The invention contemplates in one embodiment the use of an aqueous or emollient medium having one or more pH raising ingredients in a composition specifically designed to deliver oxygen to the skin's surface.

1 Claim, No Drawings

METHODS AND COMPOSITIONS FOR OXYGENATION OF SKIN TO TREAT SKIN DISORDERS

CROSS REFERENCE TO RELATED APPLICATIONS

Not applicable.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

REFERENCE TO A SEQUENCE LISTING

Not applicable.

FIELD OF THE INVENTION

This invention relates to methods and compositions for oxygenating the skin in order to treat skin disorders.

BACKGROUND OF THE INVENTION

The ability to provide oxygen to skin tissue is critical for many medical conditions including diaper rash, decubitus ulcers, diabetic ulcers, burns, and wounds. Insufficient oxygenation of compromised tissue will result in slow healing, infections, scar development, and in the worst cases, tissue death and amputation.

The effect of oxygen tension on wound healing has been extensively studied. (For a review, see Whitney, J. D. (1989)). Wound healing is dependent upon several processes including proliferation of fibroblasts, collagen synthesis, angiogenesis and re-epithelialization. Animal studies have shown that several of these processes are affected by the subcutaneous partial pressure of oxygen ($pO_2$). For example, supplemental oxygen can lead to increased rate of collagen deposition, epithelialization and improved healing of split thickness grafts. Increased subcutaneous $pO_2$ has also been shown to improve bacterial defenses.

Various methods of administration of oxygen gas, either through inhalation of the gas, or by topical treatment with the gas have been disclosed, including administering oxygen gas to a patient in a hyperbaric chamber.

Dermatitis develops when the skin is subjected to conditions that breakdown the corneum stratum. The stratum corneum is the outer layer of skin and is composed in adults of about 25 to 30 layers of keratinocytes. The main purpose of this part of the skin is to reduce water loss, repel microbial infection, protect deeper layers, and provide a water-repellant layer. Damage to this layer can occur, for example, when an infant's skin is exposed for long periods to urine and feces, these waste products lower the skin pH and result in the breakdown of the stratum corneum, which is thinner in infants compared to adults. Although moisture alone will loosen this layer and allow for friction irritation to occur, urine breakdown by fecal enzymes can reduce, or acidify, the skin resulting in chemical irritation. Decubitus ulcers can occur when patients must spend long periods in bed, and the resulting pressure points on the skin cause irritation lesions, commonly called bedsores. Some studies have shown that 8-40% of intensive care patients suffer from decubitus ulcers. According to a 2004 study, the incidence rate for decubitus ulcers calculated 474,692 new cases per year, with 34,320 deaths resulting therefrom. Another study calculated that 8% of spinal cord patients died as a result of decubitus ulcers and their complications.

The wound healing process, depending on the type of injury to the skin, is an intricate process that involves the steps of inflammation, proliferation, and remodelling. During inflammation, bacteria and debris are phagocytized and removed, and factors are released that cause the migration and division of cells involved in the proliferative phase.

The proliferative phase is characterized by angiogenesis, deposition of collagen, formation of granular tissue, re-epithelialization, and wound contraction. In angiogenesis, new blood vessels are formed by vascular endothelial cells. In fibroplasia and formation of granular tissue, fibroblasts grow and form a new, provisional extracellular matrix (ECM) by excreting collagen and fibronectin.

Simultaneously, re-epithelialization occurs, providing a new epithelial layer. It is at this stage that oxygenation of the skin is critical to wound healing.

In the remodeling phase, collagen is remodeled and realigned along tension lines and cells that are no longer needed are removed by apoptosis.

Common treatments include use of zinc oxide pastes, powders, petroleum-based creams, and even mild steroid creams to reduce excess moisture, provide antibacterial activity or barriers, and to reduce damage caused by the body's own inflammatory processes. Similar treatments are used in hospital settings to treat adult patient decubitus ulcers.

While some treatments have focused on an antibacterial approach or an approach of keeping skin dry, other have focused on pH. For example, U.S. Pat. No. 6,805,875, to Bartels, discloses topical compositions and treatments of a skin condition commonly known as "diaper rash" and more particularly, acidic-type diaper rash and other skin irritations caused by acidic bodily secretions, usually resulting from teething, antibiotic dosages, bacterial infections, and an acidic diet.

U.S. Pat. No. 6,423,323 to Neuborg, discloses a foam skin cream made by mixing a two-phase mixture of fatty acids and moisturizers with a propellant, the foam is adjusted to pH 7.6 to 8.2.

Oxygenation was disclosed in U.S. Reissue 37,274 to Gardner discloses a multi-step skin treatment to reduce aging effects that includes, in sequence, exfoliation, cleansing, hydration, and oxygenation. Exfoliation is by treating with alkaline, then acidic solutions, cleansing and hydrating is by applying various solutions, and oxygenation is disclosed as being accomplished using a tank of oxygen and a misting device.

U.S. Pat. No. 5,336,209 to Porzilli discloses a multilayer dressing which allows for increased ventilation. The removal of the top dressing is stated to increase the rate of oxygenation, improving the rate of epidermal healing.

U.S. Pat. No. 6,649,145 to McGrath, discloses methods and compositions for increasing oxygen levels by adminstering superoxygenated compositions, e.g. compositions that contain microbubbles of oxygen to increase the level to 55-220 ppm oxygen in a low temperature composition.

Accordingly, there is still a need for methods and compositions for treating skin injuries that increase the oxygen delivery to the skin in a convenient and efficient manner.

BRIEF SUMMARY OF THE INVENTION

Methods and compositions for treating wounds, decubitus ulcers, diaper rash, burns, abrasions, and other irritations and relevant injuries are provided. The invention contemplates in one embodiment the use of an aqueous or emollient medium having one or more pH raising ingredients in a composition specifically designed to deliver oxygen to the skin's surface.

In one preferred embodiment, there is provided a method for topically increasing the oxygenation of damaged epidermis, comprising the step of topically applying a dermatologically acceptable composition having a pH within a range of about pH 7.5 to about 10.4.

In another preferred embodiment, there is provided a method for topically increasing the oxygenation of damaged epidermis, comprising the step of topically applying a dermatologically acceptable composition having a pH within a range of about pH 8.2 to about pH 10.1. In one preferred embodiment, the pH is about 8.2, and in a second preferred embodiment, the pH is about 9.2.

In another preferred embodiment, there is provided wherein the dermatologically acceptable composition is an aqueous composition comprising water (Aqua) 30-100% wt., a pH adjusting component 0.1%-53.0%, at least one emollient 14%-43% wt., at least one emulsifier 3.0%-10% wt., wherein the concentration of pH adjusting component adjusts the pH of the composition within a range of about pH 7.5 to about pH 10.1, and wherein weight % is based on the total weight of the composition and the weight percentages of all components in the composition totals 100%.

In another preferred embodiment, there is provided wherein the pH adjusting component is selected from the group consisting of magnesium hydroxide 0.1%-7.0%, aluminum hydroxide 0.1%-7.0%, sodium bicarbonate 0.1%-30.0%, calcium carbonate, sodium hydroxide, cesium chloride, lactic acid, citric acid, and triethanolamine.

In another preferred embodiment, there is provided a dermatological composition, comprising water (Aqua) 30-100% wt., a pH adjusting component 0.1%-53.0% wherein the pH adjusting component is selected from the group consisting of magnesium hydroxide, aluminum hydroxide, sodium bicarbonate, calcium carbonate, sodium hydroxide, cesium chloride, lactic acid, citric acid, and triethanolamine, at least one emollient 14%-43% wt., at least one emulsifier 3.0%-10% wt., wherein the concentration of pH adjusting component adjusts the pH of the composition within a range of about pH 7.5 to about pH 10.1, wherein the dermatological composition is in the form of a cream or an ointment, and wherein weight % is based on the total weight of the composition and the weight percentages of all components in the composition totals 100%.

In another preferred embodiment, there is provided a dermatological composition, comprising Water (Aqua) 30-100% wt. and the following components in the following component weight ranges Mineral Oil 10%-30% wt., Petrolatum 3.0%-10% wt., Sorbito 13.0%-10% wt., Ceresine Wax 3.0%-10% wt., Sorbitan Sesquioleate 3.0%-10% wt., Lanolin Alcohol 1.0%-3.0% wt., Dimethicone 1.0%-3.0% wt., and Magnesium Hydroxide 0.1%-7.0% wherein the concentration of Magnesium Hydroxide adjusts the pH of the composition within a range of about pH 7.5 to about pH 10.1, and wherein weight % is based on the total weight of the composition and the weight percentages of all components in the composition totals 100%.

In another preferred embodiment, there is provided a dermatological composition, comprising Water (Aqua) 30-100% wt. and the following components in the following component weight ranges Mineral Oil 10%-30% wt., Petrolatum 3.0%-10% wt., Sorbito 13.0%-10% wt., Ceresine Wax 3.0%-10% wt., Sorbitan Sesquioleate 3.0%-10% wt., Lanolin Alcohol 1.0%-3.0% wt., Dimethicone 1.0%-3.0% wt., Aluminum Hydroxide 0.1%-7.0% wt., Magnesium Hydroxide 0.1%-7.0% wt., BHT 0.1%-1.0% wt., Phenoxyethanol 0.1%-1.0% wt., Ethylhexylglycerin 0.1%-1.0% wt., wherein the concentration of Magnesium Hydroxide, Aluminum Hydroxide, or both, adjusts the pH of the composition within a range of about pH 7.5 to about pH 10.1, and wherein weight % is based on the total weight of the composition and the weight percentages of all components in the composition totals 100%.

In another preferred embodiment, there is provided these compositions in the form of lotion, cream, emulsion, suspension, ointment, gel, bath, soak, spray, infused dressing, powder, or foam.

In another preferred embodiment, the compositions are in a delivery vehicle selected from a single use, individualized, sterile packets, a pre-soaked bandage or dressing, an undergarment treatment, a pre-soaked wipe, an infused film for application to the skin, or an infused sponge with applicator stick for use in oral care to treat mouth sores.

In another preferred embodiment, the compositions are formulated in combination with an additional therapeutic agent.

In another preferred embodiment, there is provided a method for treating a skin condition, comprising the step of topically applying a dermatologically acceptable composition having a pH within a range of about pH 7.5 to about pH 10.1. In one preferred embodiment, the pH is from about 8.2 to about 10.1, and in another preferred embodiment is from about pH 9.2 to about pH 10.1.

In another preferred embodiment, there is provided the method wherein the dermatologically acceptable composition is an aqueous composition comprising water (Aqua) 30-100% wt., a pH adjusting component 0.1%-7.0%, at least one emollient 14%-43% wt., at least one emulsifier 3.0%-10% wt., wherein the concentration of pH adjusting component adjusts the pH of the composition within a range of about pH 7.5 to about pH 10.1, and wherein weight % is based on the total weight of the composition and the weight percentages of all components in the composition totals 100%.

In another preferred embodiment, there is provided the method wherein the pH adjusting component is selected from the group consisting of magnesium hydroxide, aluminum hydroxide, sodium bicarbonate, calcium carbonate, sodium hydroxide, cesium chloride, lactic acid, citric acid, acetic acid and triethanolamine.

In another preferred embodiment, there is provided a method of treating a skin condition, comprising topically applying an effective amount of the compositions herein to a patient having said skin condition.

In another preferred embodiment, there is provided a lotion, cream or ointment, consisting essentially of the dermatological compositions herein.

DETAILED DESCRIPTION OF THE INVENTION

Methods and compositions for treating wounds, decubitus ulcers, diaper rash, burns, abrasions, and other irritations and relevant injuries are provided. The invention contemplates in one embodiment the use of an aqueous or emollient composition having one or more pH raising ingredients in a composition specifically designed to deliver oxygen to the skin's surface.

In a preferred embodiment, the pH of the composition ranges from about 7.5 to about 10.4, and more preferably from about 9.2 to about 10.1. In another preferred embodiment, the pH ranges from about pH 8.0 to about pH 10.1. In a most preferred, there is provided a pH 8.2 and a pH 9.2 composition.

In a preferred embodiment as an ointment, the medium is comprised of one or more pH raising components selected from sodium bicarbonate, calcium carbonate, magnesium hydroxide, aluminum hydroxide, sodium hydroxide, and/or cesium chloride. Additional pH adjusters contemplated herein include lactic acid, citric acid, acetic acid, and triethanolamine. In preferred embodiments where it is MgOH, the wt. is at 0.1%-7.0%, 0.1%-1.0%, or 0.75%. In preferred embodiments where it is AlOH, the wt. is at 0.1%-7.0%, 0.1%-1.0%, or 0.75%. In preferred embodiments where it is $Na(CO_2)_3$, the wt. is at 0.1%-30.0%, or 0.1%-15.0%.

In a preferred embodiment, the emollient base contains a range of at least 50% water and/or non-occlusive humectants. In a preferred embodiment, the composition is 70%-80% water. In another preferred embodiment, the composition is 70%-72% water. These may act as permeability enhancers and/or carriers for the pH raising component.

Emollients contemplated herein include natural and man-made materials, including mineral oil 10-30% wt., petrolatum 3-10% wt., sorbitol 0-20% wt. including specifically the range of 3-10% wt., dimethicone 0-7% wt. including 1-3% wt., cyclomethicone 1-3% wt., isopropyl myristate 0.1-10% wt., lactic acid 0.1-10% wt., sodium lactate 0.1-5% wt., sodium hyaluronate 0.25-2% wt., and glycerin.

Emulsifiers contemplated herein include sorbitan sesquioleate 0-15% wt., polysorbate 20, propylene glycol, carbomer incl. carbomer 940, emulsifying wax NF, ceresin, microcrystalline wax, waxes used in cosmetics, glyceryl monostearate, starch, palm stearic acid, trienthanolamine, and xanthan gum.

Additional binders, stabilizers, preservatives, colorants, and fragrances, known to a person of ordinary skill in the art, are contemplated as within the scope of this invention. Some preferred additional ingredients include, as examples without being limited thereto, lanolin alcohol 0-15% wt. including 1-3% wt., phenoxyethanol 0-5% wt. including 0.1%-1.0% wt., ethylhexylglycerin 0-5% including specifically the range of 0.1%-1.0% wt., and BHT 0.1%-1.0% wt.

Although not to be limited by an particular theory, it is believed that the alkaline environment and alkaline chemistry act as the source of the oxygen that is provided to the tissues to effectuate the treatment of the wound. Where MgOH is provided, it acts to raise the pH. Where AlOH is also added to MgOH, the AlOH appears to provide for a slow release delivery. It is believed that, in addition to its other properties, the dimethicone is reducing the surface tension of the generated oxygen and allowing for longer contact of the raised pH composition with the skin.

The ointments, creams, and salves contemplated herein may be an oil-in-water (OW) emulsion or a water-in-oil (WO) emulsion. The oil phase ingredients are mixed. Heat may be required of wax-blends. The water phase ingredients are also mixed. Processing for an oil-in-water emulsion starts with blending at high speed the water phase and the oil phase is added slowly to allow the emulsion to form. Processing for a water-in-oil emulsion is accomplished by adding the water phase to the oil phase during high speed blending to allow the emulsion to form.

To facilitate understanding of the invention set forth in the disclosure that follows, a number of terms are defined herein.

The term "wound" used herein refers broadly to injuries to the skin and subcutaneous tissue initiated in any one of a variety of ways (e.g., pressure sores from extended bed rest, wounds induced by trauma, cuts, ulcers, burns and the like) and with varying characteristics. Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that exhibits impaired healing parameters interfering with the physiological sequence of events. These wounds tend to prolong and/or halt healing time course, subjecting the wounds to further complications such as recurrent infections and necrosis.

The present invention contemplates treating all skin wound types and of all grades, including deep wounds and chronic wounds, as well as skin damage.

The term "skin wound" refers to any type of epithelial wound including, but not limited to, an ulcer such as a diabetic ulcer, a pressure ulcer, a diabetes-related wound, a burn, a sun burn, an aging skin wound, an inflammatory disease wound, a skin blistering wound, a psoriasis wound, a diabetic wound, a laceration, a surgical incision wound, and a post surgical adhesions wound.

The term "skin damage" as used herein refers to any type of skin damage or condition such as, for example, inflammation, irritation, abrasions, cuts, burns, rashes, scrapes, wounds, auto-immune related damage, infection related damage, and other types of breakdown of the stratum corneum, epidermis, and underlying tissues.

The term "epidermis" refers to the outer most layer of the skin.

Dermatological compositions of the invention may be utilized for treatment of a wide variety of dermal conditions and adverse physiological states manifesting dermally, including, without limitation, incontinence dermatitis, decubitus skin ulcers, dry skin/xerosis, psoriasis, ichthoyosis, keratosis, keratoderma, dermatitis including but not limited to pediatric diaper dermatitis, geriatric bedsores, seborrheic dermatitis, contact dermatitis, chemical injury, burns from heat, chemicals, electricity, sunlight or radiation, itching, pruritis, eczema, callouses, and burn wounds.

The term "healing" in respect to a wound or a skin damage refers to a process to repair a wound, or to repair the skin damage.

The phrase "inducing or accelerating a healing process of a skin wound or skin damage" refers to either the induction of the formation of granulation tissue of wound contraction and/or the induction of repithelialization (i.e., the generation of new cells in the epithelium). Wound healing is conveniently measured by decreasing wound area.

As used herein, the phrase "pharmaceutical composition" refers to a preparation of one or more of the active ingredients described herein with other chemical components such as physiologically suitable carriers and excipients. The purpose of a pharmaceutical composition is to facilitate administration of a composition to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of an administered active ingredient. An adjuvant is included under these phrases.

The term "excipient" as used herein refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The various compositions of the invention may be in the form of lotions, creams, emulsions, suspensions, ointments, gels, baths, soaks, sprays, infused dressing, powder, foam, or other suitable forms capable of administration to the skin of a user. Accordingly, compositions in which water and/or water-miscible solvents are employed in varying amounts, are contemplated. Additionally, the compositions may be formulated with adjuvants, additional active ingredients and/or excipients, and/or other ingredients, to impart specific thixotropy, viscosity, flow, spreading, self-leveling, or other characteristics thereto, as necessary or desirable in specific formulations.

The term "cream" refers to a topical medication form that is an emulsion of oil and water in approximately equal proportions.

The term "ointment" refers a topical medication form that is an oil and water mixture of about 80% oil and about 20% water, without being limited to specific percentages.

The term "lotion" refers to a topical medication form that is low to medium viscosity emulsion, including an oil-in-water emulsion or a water-in-oil emulsion.

The term "gel" refers to a topical medication form that liquifies upon contact with skin.

The term "paste" refers to a topical medication form that is a combination of oil, water, and a powder, i.e an ointment in which the powder is suspended.

Compositions of the invention are usefully employed as skin moisturizers, skin softening agents, skin debridement agents, etc., as well as base composition for cosmetic formulations, as well as base compositions for therapeutic, e.g., pharmacological, formulations. In cosmetic formulations, the compositions of the invention may be used with added ingredients that are solely cosmetic. Alternatively, the cosmetic formulation may include ingredients that are both cosmetically efficacious and therapeutically effective, e.g., so-called "cosmeceutical" ingredients.

In therapeutic formulations, the compositions of the invention may be utilized as base compositions for topical administration of therapeutic agents such as wound healing agents, anti-inflammatory agents, e.g., non-steroidal anti-inflammatory agents, glucocorticosteroids (e.g., hydrocortisone, triamcinolone, betametamethasone, or their respective derivatives, or ibuprofen, ketoprofen, methyl salicylate, etc.), anti-infective (antibiotic) agents (e.g., bacitracin, polymixin B, mupirocin, neomycin, and mixtures thereof), enzymes, anti-fungal agents, anti-viral agents, acne-combating agents, rosacea-combating agents, dermatitis-combating agents, topical immunomodulator agents, etc., as well as any other agents that are beneficially applied to the skin to treat or ameliorate symptoms of physiological disorders and disease states susceptible to such treatment or amelioration, such as for example, zinc oxide.

Set out below is a tabulation of secondary therapeutic agents by category and specific examples, without limitation, for which dermatological compositions of the invention may be utilized in therapeutic formulations. In the use of such therapeutic agents, the composition of the invention as variously described herein, comprising humectant, emollients and optional additional excipients, is utilized as a base to which the therapeutic agent is added in a therapeutically effective amount to yield a corresponding therapeutic composition for combating the appertaining disease state or adverse physiological condition constituting the specific indication.

Wound Healing

Papain, trypsin, allantoin, chymo-trypsin, streptokinase, streptodornase, ficin, pepsin, carboxypeptidase, amino-peptidase, chymopapain, bromelin.

Anti-Inflammatory

Hydrocortisone, triamcinolone, betametamethasone, ibupropfen, ketoprofen, methyl salicylate, dexamethasone, prednisolone, cortisone, prednisone, beclomethasone, betamethasone, flunisolide, fluocinolone acetonide, fluocinonide, indomethacin, diclofenac sodium, mefenamic acid, azulene, phenacetin, isopropylantipyrine, acetaminophen, bendzac, phenylbutazone, flufenamic acid, sodium salicylate, salicylamide, sasapyrine, etodolac.

Anti-Infectives

Bacitracin, polymixin B, mupirocin, neomycin, tetracyclines (chlortetracycline hydrochloride, oxytetracycline hydrochloride and tetracycline hydrochoride), clindamycin, gentamicin sulfate, benzalkonium chloride, benzethonium chloride, hexylresorcinol, methylbenzethonium chloride, phenol.

Antiseptics

Thymol, Menthol, Benzalkonium Chloride, Chlorhexidine gluconate, and natural oils including Tea Tree Oil.

Anti-Fungals

Miconazole, econazole, tolnaftate, ketoconazole, undecylenic acid, amphotericin, carbol-fuchsin, ciclopirox, clotrimzole, haloprogin, mafenide, naftifine, nystatin, oxiconazole, silver, sulfadiazine, sulconazole, terbinafine, tioconazole, undecylenic acid Anti-Acne salicylic acid, benzoyl peroxide, Acne, rosacea, seborheic resorcinol, sulfur, dermatitis sodium sulfacetamide, retinoic acid, isotretinoin, erythromycin, zinc, retinol, citric acid, and alpha hydroxy acid.

Anti-Virals

Acyclovir, docosanol, pencyclovir, cidofovir, desciclovir, famciclovir, ganciclovir, lobucavir, PMEA, valacyclovir, 2242, PAA, PFA, H2G, sorivudine, trifluridin, tromantadine, adenine, arabinoside, arabinosyladenine-monophosphate, lobucavir.

Topical Immunomodulators

Pimecrolimus, tacrolimus, muramyl dipeptide, cyclosporins, interferons (including alpha, beta, and gamma interferons), interleukin-2, cytokines, tumor necrosis factor, pentostatin, thymopentin, transforming factor $beta_2$, erythropoetin.

As used herein, references to compositional ingredients in percents by weight refers to weight percentages based on the total weight of the composition or formulation.

The compositions of the present invention may be packaged in both large and smaller volume containers. In one embodiment, the composition is provided in single use, individualized, sterile packets. In another embodiment, the composition is provided in a pre-soaked bandage or dressing, an undergarment treatment esp. for incontinence dermatitis, a pre-soaked wipe, or an infused film for application to the skin.

In another embodiment, the composition is provided in an infused sponge with applicator stick, esp. for use in oral care to treat mouth sores.

EXAMPLES OF COMPOSITIONS

Example 1

CB1902-178

Water (Aqua) 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Magnesium Hydroxide<1%, Phenoxyethanol<1%, Ethylhexylglycerin<1%.

Example 2

NP1902-180

Water (Aqua) 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Aluminum Hydroxide<1% wt., Magnesium Hydroxide<1%, BHT<1% wt., Phenoxyethanol<1%, Ethylhexylglycerin<1%.

Example 3

Water (Aqua) 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Magnesium Hydroxide 0.1-7.0%, Phenoxyethanol<1%, Ethylhexylglycerin<1%.

Example 4

Water (Aqua) 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Aluminum Hydroxide 0.1-7.0% wt., Magnesium Hydroxide 0.1-7.0, BHT<1% wt., Phenoxyethanol<1%, Ethylhexylglycerin<1%.

Example 5

Water (Aqua) 30-100% wt., Mineral Oil 10-30% wt., Petrolatum 3-10% wt., Sorbitol 3-10% wt., Ceresine Wax 3-10% wt., Sorbitan Sesquioleate 3-10% wt., Lanolin Alcohol 1-3% wt., Dimethicone 1-3% wt., Sodium Bicarbonate 1-30% w/Citric acid to buffer to 9.2, Phenoxyethanol<1%, Ethylhexylglycerin<1%.

USE OF THE INVENTION

Examples of Treatment

Example 6

Incontinence Dermatitis

An 80 year old woman presenting with extremely red excoriated buttocks due to long term incontinence had been treated with various traditional creams and ointments without success. Ointment of the present invention was topically applied. Within three days of continuous treatment, the skin condition improved.

Example 7

Eczema

A resident at a skilled nursing facility presented with a severe case of eczema. The clinical manager and wound care nurse topically applied an ointment of the present invention. Within a few days, the eczema was barely visible.

Example 8

Incontinence Dermatitis

A resident at a skilled nursing facility presented with an ongoing case of incontinent dermatitis and denuded areas to the right posterior thigh. The clinical manager and wound care nurse topically applied an ointment of the present invention for one week. The affected areas were markedly improved and the wounds appeared to be healing faster.

Example 9

Mastectomy Wound

A patient presented with a mastectomy wound. An ointment of the present invention was topically applied. The wound healed.

Example 10

Pediatric Recurring Eczema

A 5 year old male patient presented with a severe case of recurring eczema. After trying other products without success, the caregiver topically applied the ointment of the present invention. After one night, the skin was dramatically improved. The cream seemed to sooth the affected skin.

Example 11

Pediatric Recurring Eczema

A 5 year old female patient presented with a severe case of recurring eczema. After trying other products without success, the caregiver topically applied the ointment of the present invention. After application, there was a tremendous difference in the skin—"it worked wonders". The product was also used on chaffed skin and successful results were obtained.

Example 12

Geriatric Eczema

A 73 year old male nursing home patient presented with a case of eczema to the chest and extremities. After trying multiple prescription creams and oral steroids without success, the caregiver topically applied the ointment of the present invention. After a few months, his skin was healed. There was no longer any red, scaling skin, nor any complaints of itching.

Example 13

Pediatric Foot Dermatitis

An 8 year old female patient presented with red, cracked, and fissured skin on the bottoms of her toes and feet. The condition had been ongoing for a few years. After trying antifungal products without success, the caregiver topically applied the ointment of the present invention every night. After one week, the cracks in the toes were healed and the feet look much better.

Example 14

Burn Wound

A 3rd grade teacher presented with a severe burn on her hand after an accident. After trying several other products without success, she topically applied the ointment of the present invention. Instantaneously upon application, the burning sensation was gone. The cream was applied daily and the hand was completely healed within three days and there was no scarring.

Example 15

Mechanical Wound

A 6 year old boy fell off and was injured by a treadmill where the belt pulled the skin off his shoulder, resulting in a multiple damaged areas including a large approx. 3"×6" wound. The mother tried multiple first aid items with no success, and the boy started developing a fever and antibiotic creams were applied without success. Dressings were causing further damage to the skin. A composition of pH 9.2 was applied in 3 applications, 4 hours apart. The skin healed within one week from open wound to pink, regenerated skin.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

I claim:

1. A method for treating a severe skin wound characterized by injury to the skin and the subcutaneous tissue, comprising the step of topically applying to a patient having said severe skin wound a dermatologically acceptable composition comprising Water and the following components in the following component weight ranges Mineral Oil 10%-30% wt., Petrolatum 3.0%-10% wt., Sorbitol 3.0%-10% wt., Ceresine Wax 3.0%-10% wt., Sorbitan Sesquioleate 3.0%-10% wt., Lanolin Alcohol 1.0%-3.0% wt., Dimethicone 1.0%-3.0% wt., Aluminum Hydroxide 0.1%-7.0% wt., Magnesium Hydroxide 0.1%-7.0% wt., butylated hydroxytoluene 0.1%-1.0% wt., Phenoxyethanol 0.1%-1.0% wt., Ethylhexylglycerin 0.1%-1.0% wt., wherein the concentration of Magnesium Hydroxide, Aluminum Hydroxide, or both, adjusts the pH of the composition within a range of about pH 8.2 to about pH 10.1, and wherein weight % is based on the total weight of the composition and the weight percentages of all components in the composition totals 100%, wherein said severe skin wound involves tissue deeper than the epidermis and is selected from the group consisting of a diabetic ulcer, a decubitus or pressure ulcer, a surgical wound, a partial thickness wound, a deep wound, a chronic wound, and a severe burn.

* * * * *